United States Patent [19]

Zahradnik

[11] Patent Number: 4,540,576
[45] Date of Patent: Sep. 10, 1985

[54] NEUTRAL TOPICAL SODIUM FLUORIDE GEL

[75] Inventor: Robert T. Zahradnik, Waltham, Mass.

[73] Assignee: Johnson & Johnson Dental Products Company, East Windsor, N.J.

[21] Appl. No.: 573,530

[22] Filed: Jan. 24, 1984

Related U.S. Application Data

[63] Continuation-in-part of Ser. No. 404,263, Aug. 2, 1982, abandoned.

[51] Int. Cl.³ .................. A61K 7/18; A61K 33/16
[52] U.S. Cl. ............................ 424/151; 424/52
[58] Field of Search ............................ 424/52, 151

[56] References Cited

U.S. PATENT DOCUMENTS

| | | | |
|---|---|---|---|
| 3,337,412 | 8/1967 | Elbreder | 424/151 |
| 3,892,843 | 1/1975 | Muhler et al. | 424/151 |
| 4,066,745 | 1/1978 | Tomlinson et al. | 424/49 |
| 4,165,368 | 8/1979 | Gaffar | 424/52 |
| 4,238,476 | 12/1980 | Harvey | 424/52 |
| 4,254,101 | 3/1981 | Denny | 424/52 |
| 4,267,167 | 5/1981 | Weitzman et al. | 424/52 |
| 4,314,990 | 2/1982 | Denny et al. | 424/52 |
| 4,343,785 | 8/1982 | Schmolka | 424/52 |
| 4,344,931 | 8/1982 | Aguilar | 424/52 |
| 4,374,823 | 2/1983 | Harvey et al. | 424/52 |

OTHER PUBLICATIONS

JASPD, Jan.–Feb. 1975: 17–21, 36–45 (Anon) "Everything You Always Wanted to Know About Fluoride Therapy" (Neutral Topical Sodium Fluoride Gels, pp. 38, 40).

*Primary Examiner*—Shep K. Rose
*Attorney, Agent, or Firm*—Charles J. Metz

[57] ABSTRACT

A neutral topical sodium fluoride gel is disclosed which comprises a thickened aqueous solution of sodium fluoride buffered to maintain a pH of from about 6 to 8, wherein the thickener is a mixture of xanthan gum and a soluble salt of an acrylic acid polymer.

7 Claims, No Drawings

NEUTRAL TOPICAL SODIUM FLUORIDE GEL

This application is a continuation-in-part of my copending application Ser. No. 404,263, filed Aug. 2, 1982, now abandoned.

The invention relates to a neutral topical sodium fluoride gel composition useful for the control and prevention of dental caries when topically applied to erupted teeth.

BACKGROUND OF THE INVENTION

Neutral aqueous solutions of sodium fluoride were first used in the prevention of dental caries about 40 years ago. The initial clinical studies using neutral sodium fluoride were carried out by Knutson and Armstrong[1] and by Bibby[2]. In the early 1960's, acidulated phosphate fluoride ("APF") appeared to be a preferred material in that some laboratory tests by Brudevald et al.[3] indicated that the APF System gave a higher fluoride uptake than neutral sodium fluoride. Therefore, the predominant fluoride material used by dentists, hygienists, and other dental technicians since then has been the APF material. In the late 1960's, the APF material was introduced in the form of a gel. One such formulation is described by Elbreder in U.S. Pat. No. 3,337,412. Another APF gel is described by Weitzman et al., in U.S. Pat. No. 4,267,167.
(1) Public Health Rep. 58, 1701 (1943).
(2) J. Am. Dent. Assoc. 31, 317 (1944).
(3) Arch. Oral Biol. 8, 167 (1963).

Until this invention was made, as far as is known to the inventor the only pre-mixed fluoride gel intended for use by dental professionals that has been available commercially has been the APF gel. There have been disclosures in the literature of certain neutral sodium fluoride gels that apparently were either mixed by the user or by the investigator. For instance, see JASPD January-February 1975, 17–21, 36–45 (especially pages 38 and 40) (anon) "Everything You Always Wanted To Know About Fluoride Therapy", and references cited therein, especially: Englander et al., J. Am. Dent. Ass. 75: 639, 1967; Hayward et al., "Ca-A Cancer Journal For Clinicians". 13–21, April-May 1969; Cole et al., J. Dent. Res. Special Issue - Program and Abstracts 52: 246, 1973; Englander et al., J. Am. Dent. Ass. 78: 783, 1969; Carter, "Midwest Dentist," 43: 17, 1967; and Law, J. Am. Dent. Ass. 73: 835, 1966.

The only gelling agents specifically disclosed in these articles for use in neutral sodium fluoride gels are cellulose derivatives, either hydroxypropyl methyl cellulose or carboxymethyl cellulose.

Despite these disclosures in the literature of certain neutral sodium fluoride gels, the dental profession had continued to use the APF gels for topical fluoride application. This is surprising, since, from the standpoint of clinical efficacy, it is now believed that there is no significant difference between neutral sodium fluoride and APF[4], and yet there are some disadvantages to the use of the APF gel. For instance, APF has an acid etching potential for porcelain, polymer-glass composite material, and for metal bridge-work and orthodontic brackets. This could lead to staining, weakening, and reduction of polish.
(4) For review, see Ripa, Intl. Dent. J. 31, 105 (1981).

Up to now, most professional fluoride "gel" treatments have been carried out on pre-teenage children. On these patients, the acid etching potential of APF gel is not a significant problem because they have a low incidence of porcelain, composites, metal bridgework, etc. However, the dental profession has come to recognize that fluoride treatment would be beneficial to many more patients than pre-teenagers. For instance fluoride treatment to control and/or prevent caries is useful for those undergoing orthodontic treatment, children as well as adults. Because of improved preventive and treatment measures, more adults are retaining their natural teeth; therefore, coronal and root dental caries is becoming a significant health problem in the adult population[5]. Adult patients suffering from gum disease such as gingivitis and periodontal disease would benefit from fluoride treatment to retard the formation of caries in the portions of the roots of teeth that are becoming exposed because of receding gum lines. Also, people who are handicapped, people with impaired salivary flow caused by head and neck radiation, and hemophiliacs can benefit from fluoride treatment to control dental caries. However, when fluoride gel treatment is extended to such patients, the acid etching potential of APF gel can become a significant concern.
(5) U.S. National Center for Health Statistics data, 1971–1974.

The present invention is based upon the discovery that a neutral sodium fluoride gel using a specified combination of thickeners or gelling agents is particularly well adapted for use in dental caries prevention and control.

BRIEF SUMMARY OF THE INVENTION

The invention provides a thickened or viscous aqueous solution of sodium fluoride containing sufficient sodium fluoride for prophylactic treatment of the teeth, said thickened solution having a pH within the range of from about 6 to about 8, wherein the thickener is a mixture of xanthan gum and a soluble salt of poly(acrylic acid).

DETAILED DESCRIPTION OF THE INVENTION

The neutral topical sodium fluoride gel of the invention is actually a thickened solution, and is not a true gel. However, because the word "gel" is widely employed in the dental profession to refer to such materials, it will be used herein, with the understanding that the invention actually relates to a thickened solution and not to a true crosslinked "gel".

The gel of the invention includes water, sodium fluoride, thickener, and a buffer to maintain the pH within the range of from about 6 to about 8. Optionally, the composition will also contain flavoring agents, sweeteners, preservatives, and coloring agents at levels necessary to achieve the desired effects. Thus, typical ranges of proportions of the ingredients are shown in the following Table I:

TABLE I

| Basic Formulation | |
|---|---|
| Ingredient | % (w/w) |
| Water | 75.2–96.1 |
| Sodium Fluoride | 1.0–5.0 |
| Thickener | 1.0–20.0 |
| Buffer | 0.5–1.5 |
| Flavor | 0.1–0.5 |
| Sweetener | 0.1–0.3 |
| Preservatives | 0.15–0.35 |
| Coloring | 0.05–0.15 |

The thickener that is employed in the invention comprises a mixture of xanthan gum and a water-soluble salt of an acrylic acid polymer, e.g., the sodium or potassium salt of polyacrylic acid.

The thickener is added in a proportion sufficient to achieve a solution viscosity adequate to maintain a gel in an inverted mouthpiece tray applicator for up to about four minutes (typical time for a professionally applied fluoride treatment), and yet be fluid enough to have acceptable handling characteristics for the dental operator (e.g., when dispensing into a gel tray applicator). The thickener, therefore, must impart a certain degree of thixotropy to the neutral sodium fluoride formulation such that at rest the product has a thick, gel-like consistency, but under a shearing force, resulting perhaps from simple agitation, the sodium fluoride gel thins or undergoes a reversible transition to a more fluid condition.

Routine experimentation will suffice to determine the exact proportion of thickener needed to impart the above characteristics. The Example below illustrates typical proportions for the thickener.

The preferred formulation for use in the invention is shown below in Table II:

TABLE II

Preferred Formulation for the Neutral Sodium Fluoride "Gel" Composition

| Ingredient | % (w/w) |
| --- | --- |
| Water | 87.7 |
| Sodium Fluoride | 2.0 |
| Carbopol 934P (Polyacrylic acid) | 1.2 |
| Xanthan Gum | 1.2 |
| Sodium Hydroxide, 10% (aqueous) | 6.5 |
| Disodium Phosphate, Anhydrous | 0.7 |
| Flavor | 0.3 |
| Sodium Saccharin | 0.1 |
| Sodium Benzoate | 0.2 |
| Methyl Paraben | 0.05 |
| Coloring Solution | 0.05 |
| | 100.00 | pH = 7.0
Typical viscosity is 85 poises at 60 RPM and 25° C.

Carbopol 934P is polymerized acrylic acid. The aqueous sodium hydroxide is added to neutralize this material to form the sodium salt thereof.

The pH of the gel can be adjusted to the desired range by adding acids or bases such as phosphoric acid, hydrochloric acid, or sodium hydroxide, which form salts that are safe to ingest, or by the addition of ingestible buffering agents such as sodium phosphates. Disodium phosphate and monosodium phosphate are the preferred buffers. The buffer is preferred in order to maintain the pH within the desired neutral range, since absorption of carbon dioxide from air could reduce the pH of an unbuffered gel.

The thickener is employed in a proportion sufficient to impart a viscosity of from about 40 to about 200 poises to the solution tested by a Brookfield Viscometer at 60 rpm and 25° C., using Spindle No. 5. The degree of thixotropy of the gel is preferably such that the Brookfield viscosity measured at 1.5 rpm and 25° C., using Spindle No. 4, is within the range of from about 500 to about 4,000 poises.

EXAMPLE 1 AND CONTROL 1

It has been found that the thickener mixture comprising xanthan gum plus soluble salt of acrylic acid polymer exhibits a desirably high degree of thixotropy that aids in use and handling, and is also quite stable in storage. These qualities are illustrated in the following experiments in which the subject gel was compared with a similar gel that used a cellulose derivative as the thickener:

As Example 1, there was used the gel described above in Table II as the preferred formulation, and as Control 1 there was used an aqueous gel containing 1.1 weight percent sodium fluoride and 2 weight percent "methocel" (hydroxypropyl methyl cellulose). The pH values and the viscosities of the freshly prepared gels and of the gels after storage for various periods of time were measured. The results are set forth below:

TABLE III

EXAMPLE 1

| | | | Viscosity, poises, @ 25° C. | |
| --- | --- | --- | --- | --- |
| Time | Temperature | pH | 1.5 rpm | 60 rpm |
| 0 | 23° C. | 6.58 | 2040 | 88.4 |
| 4 weeks | " | — | 1960 | 83 |
| 8 weeks | " | — | — | 83.6 |
| 12 weeks | " | 6.61 | 1808 | 83 |
| 2 weeks | 38° C. | — | 1968 | 84.4 |
| 4 weeks | " | — | 2136 | 85.2 |
| 8 weeks | " | — | — | 84 |
| 12 weeks | " | 6.52 | 1960 | 84.2 |
| 2 weeks | 49° C. | — | 1800 | 83 |
| 3 weeks | " | — | 1920 | 82.8 |
| 4 weeks | " | — | 2112 | 87 |
| 8 weeks | " | — | — | 86.4 |
| 12 weeks | " | 6.49 | 2096 | 83 |

TABLE IV

CONTROL 1

| | | | Viscosity, poises, @ 25° C. | |
| --- | --- | --- | --- | --- |
| Time | Temperature | pH | 1.5 rpm | 60 prm |
| 0 | 23° C. | 7.54 | 120 | 72 |
| 10 days | " | 7.84 | 120 | 61 |
| 24 days | " | 7.57 | 116 | 60 |
| 31 days | " | 7.49 | 120 | 60.7 |
| 45 days | " | 7.78 | 130 | 60.9 |
| 7 days | 49° C. | 7.59 | 96 | 60.4 |
| 21 days | " | 7.43 | 60 | 46.3 |
| 28 days | " | 7.31 | 52 | 39.9 |
| 42 days | " | 7.32 | 31.2 | 24 |

As these data illustrate, the gel of this invention is much more stable and has a much greater degree of thixotropy than a comparable gel in which the gelling agent is a cellulose derivative.

The ratio of xanthan gum to soluble acrylic acid polymer has not been found to be narrowly critical. For instance, proportions can vary from about 10 to about 90, and preferably from about 40 to about 60, weight per cent xanthan gum, based on weight of xanthan gum plus soluble salt of acrylic acid polymer.

The thickened neutral sodium fluoride aqueous solutions of the invention are applied to the teeth by the dentist, hygienist, or technician in the conventional manner. This involves either a tray technique or a "paint on" technique. The tray technique is preferred because of the convenience and time-saving aspects of the tray application. In this method, a gel application tray is filled approximately one-third full with the gel product. After the teeth are thoroughly dried, the filled tray is inserted into the patient's mouth, and is maintained there for four minutes. The tray is then removed and the patient expectorates any excess gel remaining in the mouth. For the "paint on" technique, the teeth are isolated with cotton rolls and dried thoroughly with air. A cotton applicator is then dipped into the gel and applied to the teeth, keeping the teeth covered with gel for four minutes. Once again, after the cotton rolls are removed, the patient expectorates excess gel.

What is claimed is:

1. A thickened sodium fluoride aqueous composition suitable for use in the topical prophylactic treatment of the teeth, said composition consisting essentially of from about 75.2 to about 96.1 weight percent water, sodium fluoride in a proportion of from about 1 to about 5 weight percent of the total composition, and thickener, wherein the pH of the composition is within the range of from about 6 to about 8, and wherein the thickener consists essentially of xanthan gum and a water soluble salt of an acrylic acid polymer.

2. The composition of claim 1 wherein said composition contains a buffering agent.

3. The composition of claim 1 wherein said composition includes flavoring agents, preservatives, and coloring agents.

4. The composition of claim 2 wherein the buffering agent is disodium phosphate, monosodium phosphate, or mixture thereof.

5. The composition of claim 1, 2, 3, or 4 wherein said composition has a viscosity of from about 40 to about 200 poises tested by a Brookfield viscometer at 60 RPM and 25° C., and a viscosity of 500 to 4000 poises tested by a Brookfield viscometer at 1.5 RPM and 25° C.

6. The composition of claim 5 wherein the thickener is xanthan gum plus the sodium salt of polyacrylic acid.

7. A method for treating teeth to help control dental caries which comprises applying an effective amount of the composition of claim 1 to the surface of teeth to be treated, and leaving said composition in contact with the teeth for a period of time sufficient to effect treatment.

* * * * *